United States Patent [19]
Wright

[11] 3,987,192
[45] Oct. 19, 1976

[54] COMPOSITIONS AND PROCESS OF TREATMENT

[75] Inventor: John B. Wright, Kalamazoo, Mich.

[73] Assignee: The Upjohn Company, Kalamazoo, Mich.

[22] Filed: July 18, 1974

[21] Appl. No.: 489,620

Related U.S. Application Data

[63] Continuation of Ser. No. 431,031, Jan. 7, 1974, abandoned, which is a continuation of Ser. No. 316,976, Dec. 20, 1972, abandoned.

[52] U.S. Cl. ............................................. 424/304
[51] Int. Cl.$^2$...................................... A61K 31/275
[58] Field of Search ................................... 424/304

[56] References Cited
UNITED STATES PATENTS

| | | | |
|---|---|---|---|
| 3,852,324 | 12/1974 | Wright | 424/304 |
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

OTHER PUBLICATIONS

Bogert et al., Chemical Abstracts 5:82$^7$.
Reissert et al., Chemical Abstracts 4:206$^4$.
Berichte 42: 3710–3721 (1909).
Ciba Ltd., Chemical Abstracts 72:12413m (1970).

*Primary Examiner*—Norman A. Drezin
*Attorney, Agent, or Firm*—Martin B. Barancik; William A. Hodes; Roman Saliwanchik

[57] ABSTRACT

This invention relates to pharmaceutical compositions containing known compounds of the formula

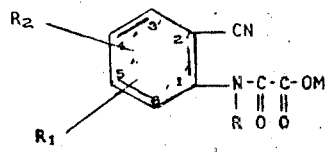

wherein M is selected from the group consisting of hydrogen, aluminum, ammonium, sodium, potassium, calcium, tris(hydroxymethyl)methylammonium and lower alkyl of 1 through 4 carbon atoms, R is selected from the group consisting of hydrogen and lower alkyl of 1 through 4 carbon atoms, and $R_1$ and $R_2$ are selected from the group consisting of hydrogen, fluorine, chlorine, bromine, trifluoromethyl, lower alkoxy of 1 through 4 carbon atoms and lower alkyl of 1 through 4 carbon atoms.

The compounds (1) above are formulated with pharmaceutical carriers for inhalation or for oral, parenteral or rectal administration, with insufflation being the preferred method. The compositions are useful in the prophylactic treatment of sensitized humans and mammals for allergic and all anaphylactic reactions of a reaginmediated and non-reagin-mediated nature.

8 Claims, No Drawings

COMPOSITIONS AND PROCESS OF TREATMENT

CROSS REFERENCE TO RELATED APPLICATIONS

This is a continuation of my application Ser. No. 431,031 filed Jan. 7, 1974 now abandoned, which is in turn a continuation of my application Ser. No. 316,976 filed Dec. 20, 1972 and now abandoned.

BRIEF SUMMARY OF THE INVENTION

This invention relates to pharmaceutical compositions of known compounds (I) and a process for the prophylactic treatment of allergic conditions employing said compositions.

The novel compositions comprise a known compound of the formula

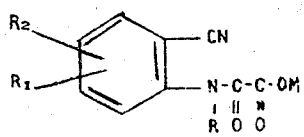

wherein M is selected from the group consisting of hydrogen, aluminum, ammonium, sodium, potassium, calcium, tris(hydroxymethyl)methylammonium and lower alkyl of 1 through 4 carbon atoms, R is selected from the group consisting of hydrogen and lower alkyl of 1 through 4 carbon atoms, and $R_1$ and $R_2$ are selected from the group consisting of hydrogen, fluorine, chlorine, bromine, trifluoromethyl, lower alkoxy of 1 through 4 carbon atoms and lower alkyl of 1 through 4 carbon atoms.

As employed in this application, the term "lower alkyl" includes methyl, ethyl, propyl, isopropyl, butyl, isobutyl, and tert. butyl; the term "lower alkoxy" includes methoxy, ethoxy, propoxy, isopropoxy, butoxy and tert. butoxy.

The known compounds (I) of this invention are prepared by the procedures described in Ber. 42, 3710 (1909). Said publication discloses that boiling o-aminobenzonitrile (also known as anthranilonitrile) with oxalic acid methyl ester, which on hydrolysis with dilute aqueous sodium hydroxide solution, yields o-(or 2'-)cyanooxanilic acid (I). The sodium, potassium or calcium salt of a 2'-cyanooxanilic acid (I) can be prepared by methods well-known in the art, e.g., by mixing said acid with sodium, potassium or calcium hydroxide and neutralizing the basic solution with an acid such as acetic acid, and recrystallizing the precipitate that forms from a medium such as 50% ethanol-water. Also, a 2'-cyanooxanilic acid (I) can be converted to its lower alkyl ester by known standard procedures, e.g., by mixing it with a corresponding lower alkanol (such as methanol, ethanol, propanol or butanol) and a dry strong mineral acid such as hydrochloric acid.

Following the procedures of the immediately preceding paragraph, but substituting another anthranilonitrile as starting material, such as 1. 5-butoxyanthranilonitrile (prepared as in Bull. Soc. Chim. Fr. 1969, 2008),
2. 5-ethoxyanthranilonitrile (ibid.),
3. 5-methoxyanthranilonitrile (ibid.),
4. N-butylanthranilonitrile (prepared as in Zh. Obschch. Khim. 33, 3777),
5. 5-bromoanthranilonitrile (prepared as in J. Org. Chem. 26, 4967),
6. 4-chloroanthranilonitrile (prepared as in J. Amer. Chem. Soc. 69, 940),
7. 5-chloroanthranilonitrile (prepared as in J. Chem. Soc. 1959, 1633),
8. 6-chloro-N-methylanthranilonitrile (prepared as in Ann. 716, 47),
9. 3,6-dichloroanthranilonitrile (ibid.),
10. 3,6-dimethylanthranilonitrile (prepared as in Indian J. Chem. 1, 249),
11. 6-ethylanthranilonitrile (prepared as in German Pat. No. 1,125,939),
12. N-methylanthranilonitrile (prepared as in J. Org. Chem. 17, 2622),
13. 4-methylanthranilonitrile (prepared as in J. Chem. Soc. 1959, 1633),
14. 5-methylanthanilonitrile (prepared as in Netherlands Patent Application No. 65/07782),
15. 6-methylanthranilonitrile (prepared as in British Pat. No. 901,977),
16. 4-bromo-6-methylanthranilonitrile (prepared as in U.S. Pat. No. 1,774,650),
17. 4-chloro-6-methylanthranilonitrile (ibid.),
18. 3,5-dibromoanthranilonitrile (prepared as in German Pat. No. 928,902),
19. 5-methoxyanthranilonitrile (prepared as in J. Org. Chem. 20, 1654),
20. 6-methoxyanthranilonitrile (prepared as in Ann. 388, 23),
21. 3,5-dichloro-N-methylanthranilonitrile (prepared as in Ann. 716, 47),
22. 2,5-di-tert.-butylanthanilonitrile (prepared as in Helv. Chim. Acta. 50, 2244),
23. 4-propoxyanthranilonitrile (prepared as in U.S. Pat. No. 1,774,650),
24. 4-trifluoromethylanthranilonitrile,
25. 3-tert. butylanthranilonitrile (prepared as in Ber. 98, 1577), and the like, yields, respectively, 1. 4'-butoxy-2'-cyanooxanilic acid (I),
2. 2'-cyano-4'-ethoxyoxanilic acid (I),
3. 2'-cyano-4'-methoxyoxanilic acid (I),
4. N-butyl-2'-cyanooxanilic acid (I),
5. 4'-bromo-2'-cyanooxanilic acid (I),
6. 5'-chloro-2'-cyanooxanilic acid (I),
7. 4'-chloro-2'-cyanooxanilic acid (I),
8. 3'-chloro-2'-cyanooxanilic acid (I),
9. 2'-cyano-3',6'-dichlorooxanilic acid (I),
10. 2'-cyano-3',6'-dimethyloxanilic acid (I),
11. 2'-cyano-3'-ethyloxanilic acid (I),
12. 2'-cyano-N-methyloxanilic acid (I),
13. 2'-cyano-5'-methyloxanilic acid (I),
14. 2'-cyano-4'-methyloxanilic acid (I),
15. 2'-cyano-3'-methyloxanilic acid (I),
16. 5'-bromo-2'-cyano-3'-methyloxanilic acid (I),
17. 5'-chloro-2'-cyano-3'-methyloxanilic acid (I),
18. 2'-cyano-4',6'-dibromooxanilic acid (I),
19. 2'-cyano-4'-methoxyoxanilic acid (I),
20. 2'-cyano-3'-methoxyoxanilic acid (I),
21. 2'-cyano-4',6'-dichloro-N-methyloxanilic acid (I),
22. 2'-cyano-4',6'-di-tert. butyloxanilic acid (I),
23. 2'-cyano-5'-propoxyoxanilic acid (I),
24. 2'-cyano-5'-trifluoromethyloxanilic acid (I),
25. 2'-cyano-5'-tert. butyloxanilic acid (I), and the like, in addition to an aluminum, ammonium, sodium, potassium, calcium or tris(hydroxymethyl)ammonium salt or a lower alkyl ester thereof.

The compounds (I) of the compositions of this invention have anti-allergenic (especially anti-asthmatic) activity, inhibiting a positive Passive Cutaneous Anaphylactic (PCA) test induced by the rat immunochemical counterpart of human IgE (reagin), considered indicative of allergic activity. This activity is apparent when these compounds are tested for their inhibition of the rat's PCA reaction. The PCA assay is described by I. Mota in Ann. N.Y. Acad. Sci. 103, 264 ([1963).

DETAILED DESCRIPTION

The following examples are illustrative of the manner of making the novel compositions and using them in the process of this invention, and set forth the best mode contemplated by the inventor of carrying out his invention, but are not to be construed as limiting the scope thereof.

The compositions of the present invention are presented for administration to humans and animals in unit dosage forms, such as tablets, capsules, pills, powders, granules, rectal suppositories, sterile parenteral solutions or suspensions, and oral solutions or suspensions, and oil-in-water and water-in-oil emulsions containing suitable quantities of the compound of Formula I. The preferred method of administration is inhalation into the lung by means of a liquid aerosol or powder for insufflation.

For oral administration either solid or fluid unit dosage forms can be prepared. For preparing solid compositions such as tablets, the compound of Formula I is mixed with conventional ingredients such as talc, starch, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweetners such as sugar and saccharin, together with an aromatic flavoring agent.

Suspensions can be prepared in an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a loca, anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The preferred compositions are those adapted for inhalation into the lung and containing a water soluble form of a compound of the Formula I.

Compositions for inhalation are of three basic types: 1) a powder mixture preferably micro-pulverized; 2) an aqueous solution to be sprayed with a nebulizer; and 3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of Formula I (where M is sodium, potassium or tris(hydroxymethyl)methylammonium in water and adding salt to provide an isotonic solution and buffering to a pH compatible with inhalation. The solutions are dispersed in a spray device or nebulizer and sprayed into the mouth while inhaling.

Aerosols are prepared by dissolving a compound of Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal or cosmetic use, the liquedified propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Suitable liquefied propellants are the fluorinated and fluorochlorinated lower alkanes such as are sold under the trademarks "Freon" and "Genetron". Mixtures of the abovementioned propellants may suitably be employed. Examples of these propellants are dichlorodifluoromethane (Freon 12) dichlorotetrafluoroethane (Freon 114). trichloromonofluoromethane (Freon 11), dichloromonofluoromethane (Freon 21), monochlorodifluoromethane (Freon 22), trichlorotrifluoroethane (Freon 113), difluoroethane (Genetron 142-A) and monochlorotrifluoromethane (Freon 13). Alternatively, the inhalation compositions of this invention can be dispersed from pressure-loaded vessels, e.g., by use of compressed air or carbon dioxide cartridges.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, chachets, teaspoonfuls, tablespoonfuls, dropperfuls, ampuls, vilas, aerosols with metered discharges, segregated multiples of any of the foregoing, and other forms as herein described.

The dosage of the compound of Formula I for treatment depends on the route of administration. A dosage schedule of from about 0.01 to 50 mg. in a single dose, administered parenterally or by inhalation, embraces the effective range for preventing allergic attack for which the compositions are effective. The dosage to be administered is repeated up to 4 times daily. The oral dose is from about 0.1 to about 500 mg. in a single dose.

Alternatively, the compounds of Formula I in suitable pharmaceutical compositions can be administered first as a priming dose to adequately mitigate and control the allergic symptoms, followed by maintenance doses consisting of dosages of much reduced amounts of drugs, e.g., from about 1/200th to about 1/10th of the amounts of drug of the priming dose, preferably from about 1/50 th to about 1/20 th, in a suitable pharmaceutical composition and at suitable intervals, e.g., 4 times daily, to maintain the anti-allergic prophylaxis, as prescribed by the attending physician.

The administration of the compositions of the present invention to humans and animals provides a method for the prophylactic treatment of allergy or all anaphylactic reactions of a reagin-mediated and non-reagin-mediated nature. That is to say, these compositions when administered to a sensitized individual prior to the time that the individual comes into contact with substanced to which he is allergic, the compositions will prevent the allergic reaction which would otherwise occur.

For example, the process can be used for prophyactic treatment of such chronic conditions as bronchial asthma, allergic rhinitis, food allergy, hay fever, articaria, and auto-immune diseases.

EXAMPLE 1

A lot of 10,000 tablets, each containing 0.1 mg. of 2'-cyanooxanilic acid (I), is prepared from the following types and amounts of ingredients:

| 2'-Cyanooxanilic acid (I) | 1 Gm. |
| Dicalcium phosphate | 1,500 Gm. |
| Methylcellulose, U.S.P. (15 cps.) | 60 Gm. |
| Talc | 150 Gm. |
| Corn Starch | 200 Gm. |
| Calcium Stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed throughly with the talc, starch and magnesium stearate, and compressed into tablets.

These tablets are useful in preventing hay fever attacks at a dose of 1 tablet every 4 hours.

EXAMPLE 2

One thousand two-piece hard gelatin capsules, each containing 100 mg. of 2'-cyanooxanilic acid (I) are prepared from the following types and amounts of ingredients:

| 2'-Cyanooxanilic acid (I), micronized | 100 Gm. |
| Talc | 10 Gm. |
| Magnesium Stearate | 0.5 Gm. |

The ingredients are mixed well and filled into capsules of the proper size.

Capsules so prepared are useful in preventing attacks of bronchial asthma at a dose of one capsule every 6 hours.

EXAMPLE 3

One thousand tablets, each containing 500 mg. of 2'-cyanooxanilic acid (I) are made from the following types and amounts of ingredients:

| 2'-Cyanooxanilic acid (I) | 500 Gm. |
| Microcrystalline cellulose NF | 120 Gm. |
| Starch | 16 Gm. |
| Magnesium stearate powder | 4 Gm. |

The ingredients are screened and blended together and pressed into 640 mg. tablets.

The tablets are useful to protect against food allergy at a dose of 1 tablet before meals.

EXAMPLE 4

A sterile preparation suitable for intramuscular injection and containing 1 mg. of 2'-cyanooxanilic acid (I) in each milliliter is prepared from the following ingredients:

| 2'-Cyanooxanilic acid (I) | 1 Gm. |
| Benzyl benzoate | 200 Gm. |
| Methylparaben | 1.5 Gm. |
| Propylparaben | 0.5 Gm. |
| Cottonseed oil q.s. | 1,000 Gm. |

One milliliter of this sterile preparation is injected intramuscularly for prophylactic treatment of allergic rhinitis.

EXAMPLE 5

Aqueous Solution 600 ml. of an aqueous solution containing 0.1 mg. of the 2'-cyanooxanilic acid sodium salt (I) per ml. is prepared as follows:

| 2'-Cyanooxanilic acid sodium salt (I) | 60 mg. |
| Sodium chloride | 5400 mg. |
| Water for injection q.s. | 600 ml. |

The 2'-cyanooxanilic acid sodium salt (I) and sodium chloride are dissolved in sufficient water to make 600 ml. and sterile filtered.

The solution is placed in nebulizers designed to deliver 0.25 ml. of solution per spray.

The solution is sprayed into the lungs every 4 to 6 hours for prevention of asthmatic attacks.

Following the procedure of Example 5, but substituting an appropriate amount of the tris(hydroxymethyl)aminomethane (THAM) salt of 2'-cyanooxanilic acid (I), provides an aqueous solution that can be similarly employed.

EXAMPLE 6

Powder for Insufflation

A powder mixture consisting of 100 mg. of 2'-cyanooxanilic acid (I) and sufficient lactose to make 5 grams of mixture is micropulverized and placed in an insufflator designed to deliver 50 mg. of powder per dose.

The powder is inhaled into the lungs for prevention of asthmatic attacks.

EXAMPLE 7

Aerosol

Twelve grams of an aerosol composition is prepared from the following ingredients:

| | |
|---|---|
| 2'-Cyanooxanilic acid sodium salt (I) | 0.015 Gm. |
| 50 % ethanol | 4.855 Gm. |
| Freon 12 | 1.43 Gm. |
| Freon 114 | 5.70 Gm. |

The 2'-cyanooxanilic acid sodium salt (I) is dissolved in the 50% ethanol and chilled to −30° C. and added to the chilled Freons. The 12 grams of composition is added to a 13 cc. plastic coated bottle and capped with a metering valve. The metering valve releases 80 mg. of composition in an aerosol.

The aerosol is inhaled every 4 to 6 hours for prevention of asthmatic attacks.

Following the procedure of Example 7, but substituting an appropriate amount of the THAM salt of 2'-cyanooxanilic acid (I), gives an aerosol that can be similarly employed.

The procedures described about in Examples 1 through 7 for the preparation of the compositions of 2'-cyanooxanilic acid (I), can also be employed in the production of medicaments wherein the active ingredient is another compound embraced by Formula I, e.g., 2'-cyanooxanilic acid, sodium salt (I), 2'-cyanooxanilic acid, methyl ester (I), 4'-butoxy-2'-cyanooxanilic acid (I), 4'-butoxy-2'-cyanooxanilic acid, potassium salt (I), 4'-butoxy-2'-cyanooxanilic acid ethyl ester (I), 2'-cyano-4'-ethoxyoxanilic acid (I), 2'-cyano-4'-ethoxyoxanilic acid, calcium salt (I), 2'-cyano-4'-ethoxyoxanilic acid propylester (I), 2'-cyano-4'-methoxyoxanilic acid (I), N-butyl-2'-cyanooxanilic acid (I), N-butyl-2'-cyanooxanilic acid propyl ester (I), 4'-bromo-2'-cyanooxanilic acid (I), 4'-bromo-2'-cyanooxanilic acid, potassium salt (I), 4'-chloro-2'-cyanooxanilic acid (I), 5'-chloro-2'-cyanooxanilic acid, butyl ester (I), 4'-chloro-2'-cyanooxanilic acid (I), 3'-chloro-2'-cyanooxanilic acid (I), 3'-chloro-2'-cyanooxanilic acid, methyl ester (I), 2'-cyano-3',6'-dichlorooxanilic acid (I), 2'-cyano-3',6'-dichlorooxanilic acid, potassium salt (I), 2'-cyano-3',6'-dimethyloxanilic acid (I), 2'-cyano-3',6'-dimethyloxanilic acid, ethyl ester (I), 2'-cyano-3'-ethyloxanilic acid (I), 2'-cyano-N-methyloxanilic acid (I), 2'-cyano-4'-methoxyoxanilic acid (I), 2'-cyano-4'-methoxyoxanilic acid, propyl ester (I), 2'-cyano-5'-methoxyoxanilic acid (I), 2'-cyano-3'-methoxyoxanilic acid (I), 5'-bromo-2'-cyano-3'-methoxyoxanilic acid (I), 5'-bromo-2'-cyano-3'-methoxyxanilic acid, sodium salt (I), 5'-chloro-2'-methoxyxanilic acid (I), 2'-cyano-4',6'-dibromooxanilic acid (I), 2'-cyano-4'-methoxy-5'-trifluoromethyloxanilic acid (I), 2'-cyano-4',6'-dichloro-N-methyloxanilic acid (I), 2'-cyano-4',6'-dichloro-N-methyl-oxanilic acid, calcium salt (I), 2'-cyano-4',6'-ditert. butyloxanilic acid (I), 2'-cyano-4',6'-ditert. butyloxanilic acid, butyl ester (I), 2'-cyano-5'-propoxyoxanilic acid (I), 2'-cyano-5',6'-ditrifluoromethyloxanilic acid (I), 2'-cyano-5',6'-ditrifluoromethyloxanilic acid, ethyl ester (I), 2'-cyano-6'-tert. butyloxanilic acid (I), and the like.

While the treatment of hay fever, bronchial asthma, food allergy, allergic rhinitis and asthmatic attacks disclosed following Examples 1 through 7 utilizes 2'-cyanooxanilic acid (I), similarly effective therapy is provided by employing medicaments wherein the active ingredient is another compound embraced by Formula I, e.g., 2'-cyanooxanilic acid, potassium salt (I), 4'-butoxy-2'-cyanooxanilic acid (I), 2'-cyano-4'-ethoxyoxanilic acid ethyl ester (I), 2'-cyano-4'-methoxyoxanilic acid (I), N-butyl-2'-cyanooxanilic acid (I), N-butyl-2'-cyanooxanilic acid, calcium salt (I), 2'-cyano-N-ethyloxanilic acid (I), 4'-bromo-2'-cyanooxanilic acid (I), 5'-chloro-2'-cyano-N-propyloxanilic acid (I), 4'-chloro-2'-cyano-N-ethyloxanilic acid (I), 3'-chloro-2'-cyanooxanilic acid (I), 3'-chloro-2'-cyanooxanilic acid, propyl ester (I), 2'-cyano-3',6'-dichlorooxanilic acid (I), 2'-cyano-3',6'-dimethyloxanilic acid (I), 2'-cyano-6'-ethyl-4'-methyloxanilic acid (I), 2'-cyano-3'-ethyl-5'-methyloxanilic acid (I), 2'-cyano-N-methyloxanilic acid (I), 2'-cyano-N-methyloxanilic acid, calcium salt (I), 2'-cyano-5'-fluoro-6'-ethyloxanilic acid (I), 2'-cyano-4',5'-difluroroxanilic acid, ethyl ester (I), 2'-cyano-5'-methyloxanilic acid (I), 2'-cyano-3'-methyloxanilic acid, potassium salt (I), 5'-bromo-2'-cyano-3'-methyloxanilic acid (I), 5'-chloro-2'-cyano-3'-ethyloxanilic acid, methyl ester (I), 2'-cyano-6',4'-dibromooxanilic acid (I), 2'-cyano-4'-ethoxy-3'-fluorooxanilic acid (I), 2'-cyano-5'-methoxyoxanilic acid (I), 2'-cyano-5',3'-dimethoxyoxanilic acid (I), 2'-cyano-4'-methoxy-6'-fluorooxanilic acid, sodium salt (I), 2'-cyano-6',4'-dichloro-N-methyloxanilic acid (I), 6'-bromo-4'-chloro-2'-cyano-N-ethyloxanilic acid (I), 2'-cyano-6',4'-ditert. butyloxanilic acid (I), 2'-cyano-3'-fluoro-5'-propoxyoxanilic acid, methyl ester (I), 2'-cyano-5'-ethyl-3'-methyloxanilic acid (I), 2'-cyano-3'-propyl-5'-trifluoromethyloxanilic acid (I), 2'-cyano-6',4'-difluorooxanilic acid, potassium salt (I), 2'-cyano-5'-ethoxy-3'-trifluoromethyloxanilic acid, sodium salt (I), 6'-butyl 6'-chloro-2'-cyanooxanilic acid (I), 6'-bromo-3'-butyl-2'-cyanooxanilic acid, propyl ester (I), 2'-cyano-6'-tert.-butyloxanilic acid (I), and the like.

I claim:

1. A pharmaceutical composition useful for the prophylaxis of asthma, rhinitis, food allergy and uticaria symptoms which comprises as the sole active agent an anti-asthma, rhinitis, food allergy or uticaria effective amount of a compound of the formula wherein M is selected from the group consisting of hydrogen, aluminum, ammonium, sodium, potassium, calcium, tris(hydroxymethyl)methyl ammonium and lower alkyl of 1 through 4 carbon atoms, R is selected from the group consisting of hydrogen and lower alkyl of 1 through 4 carbon atoms, and $R_1$ and $R_2$ are selected from the group consisting of hydrogen, fluorine, chlorine, bromine, trifluoromethyl, lower alkoxy of 1 through 4 carbon atoms and lower alkyl of 1 through 4 carbon atoms, in association with a pharmaceutical carrier for oral, parenteral, inhalation or rectal route of administration and in a dosage form selected from the group consisting of tablet, capsule, pill, powder for insufflation, aerosol solution for insufflation, aqueous solution, syrup, elixir, aqueous suspension, sterile aqueous solution and suspension, and suppository.

2. A pharmaceutical composition in accordance with claim 1 wherein R is hydrogen.

3. A pharmaceutical composition in accordance with claim 2 wherein said carrier is suitable for inhalation.

4. A pharmaceutical composition in accordance with claim 3 wherein said carrier is suitable for insufflation or aerosolization.

5. A method for prophylactically treating asthma, rhinitis, food allergy or uticaria in mammals which comprises administering to a mammal in need of such treatment an anti-asthma, rhinitis, food allergy or uticaria effective amount of a compound of the formula

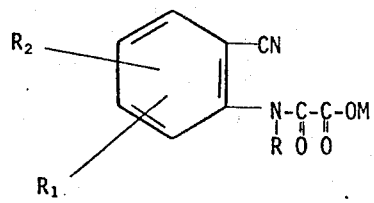

wherein M is selected from the group consisting of hydrogen, aluminum, ammonium, sodium, potassium, calcium, tris(hydroxymethyl)methyl ammonium and lower alkyl of 1 through 4 carbon atoms, R is selected from the group consisting of hydrogen and lower alkyl of 1 through 4 carbon atoms, and $R_1$ and $R_2$ are selected from the group consisting of hydrogen, fluorine, chlorine, bromine, trifluoromethyl, lower alkoxy of 1 through 4 carbon atoms and lower alkyl of 1 through 4 carbon atoms, in association with a pharmaceutical carrier.

6. A process of claim 5 comprising the specific compound wherein M, R, $R_1$ and $R_2$ are hydrogen, namely, 2'-cyanooxanilic acid.

7. A method in accordance with claim 5 wherein R is hydrogen.

8. A method in accordance with claim 7 wherein the mammal needs treatment for asthma.

* * * * *